United States Patent [19]

Ajot et al.

[11] Patent Number: 5,266,270
[45] Date of Patent: Nov. 30, 1993

[54] ON-LINE TEST AND ANALYSIS PROCESS AND EQUIPMENT MAKING IT POSSIBLE TO ESTABLISH A MATERIAL BALANCE OF A CHEMICAL REACTION

[75] Inventors: Hubert Ajot; Edouard Freund, both of Rueil Malmaison; Pierre Grandvallet, Bruyeres, all of France

[73] Assignee: Institut Francais du Petrole, Rueil Malmaison, France

[21] Appl. No.: 915,391

[22] Filed: Jul. 20, 1992

Related U.S. Application Data

[60] Continuation of Ser. No. 603,035, Oct. 25, 1990, abandoned, which is a division of Ser. No. 875,167, Jun. 17, 1986, Pat. No. 4,988,626.

[30] Foreign Application Priority Data

Jun. 17, 1985 [FR] France .................. 85 09136

[51] Int. Cl.⁵ ........................................... G01N 35/00
[52] U.S. Cl. ........................... 422/80; 422/68.1; 422/83; 422/89; 436/174; 436/181
[58] Field of Search ............ 422/68.1, 83, 80, 89; 436/174, 181

[56] References Cited

U.S. PATENT DOCUMENTS

| | | | |
|---|---|---|---|
| 3,961,896 | 6/1976 | Dunn | 422/90 |
| 3,982,897 | 9/1976 | Scheinberg | 436/181 |
| 4,670,405 | 6/1987 | Stetter et al. | 436/151 |
| 4,698,314 | 10/1987 | Tao | 436/181 |
| 4,699,886 | 10/1987 | Lelong | 436/181 |
| 4,814,281 | 3/1989 | Byers | 422/76 |
| 4,888,295 | 12/1989 | Zaromb et al. | 422/70 |
| 4,900,680 | 2/1990 | Miyazawa et al. | 422/70 |

Primary Examiner—Timothy M. McMahon
Attorney, Agent, or Firm—Millen, White, Zelano & Branigan

[57] ABSTRACT

On-line test and analysis equipment equivalent for establishing a material balance of a chemical reaction comprising: a reactor; an injection system for a charge having a certain flow and composition, connected to the reactor; instrumentation for measuring the flow and composition of the charge; a heater to heat the reactor so as to provide a gaseous effluent; first analysis instrumentation to provide a qualitative and quantitative analysis of effluents contained in sampling valves; expansion device for the effluents; second analysis instrumentation for expanded effluent; an instrument to measure the volume of the effluents connected to the outlet of the first analysis means; and instrumentation connected to the instrumentation for measuring the flow and composition of the charge, to the instrument for measuring the volume, and to the first and second analysis instrumentation, the processing instrumentation being capable of determining a material balance from the measurements of flow and composition of the charge and the analysis of the charge, and from the analysis of the effluents.

13 Claims, 2 Drawing Sheets

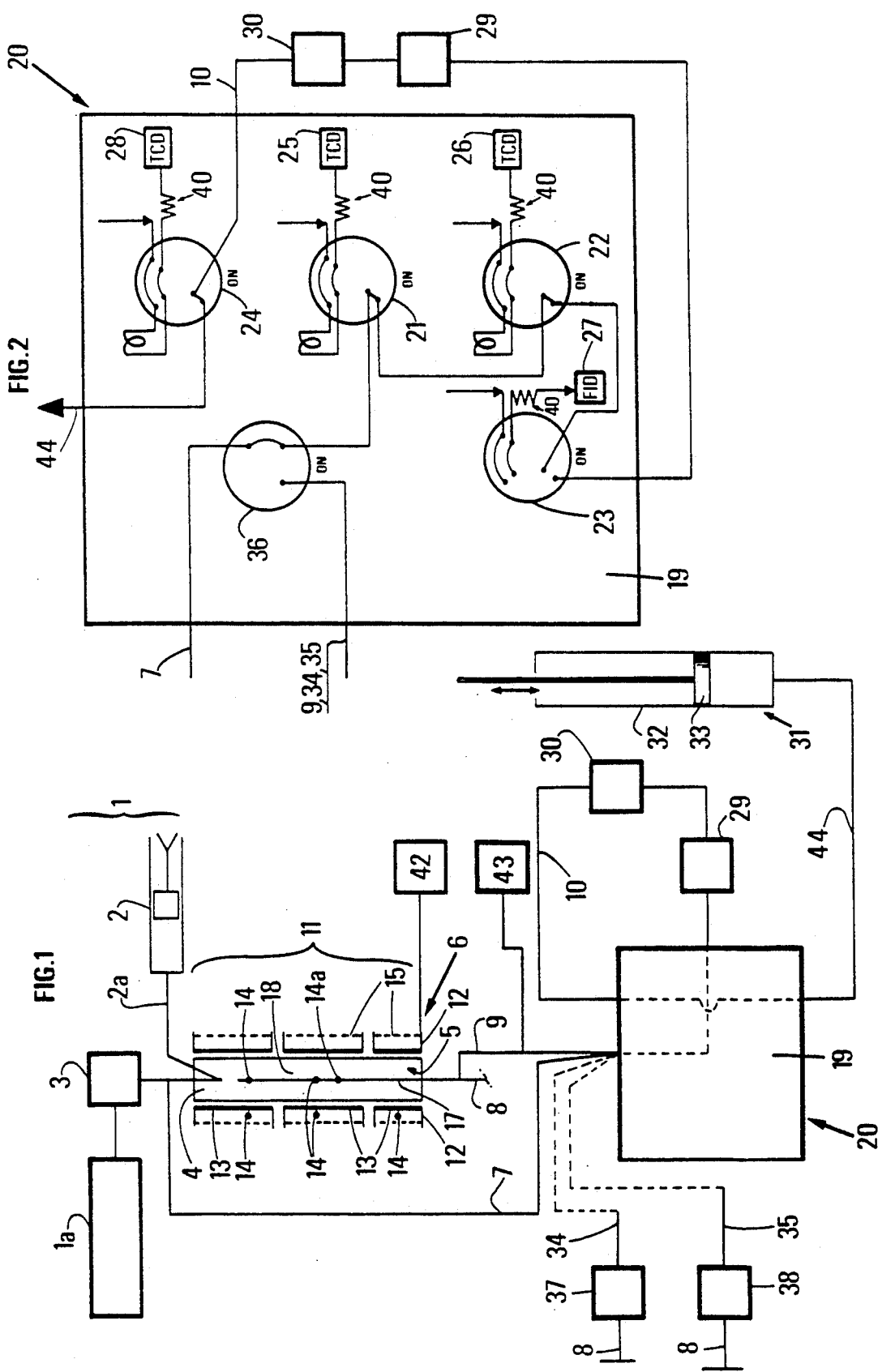

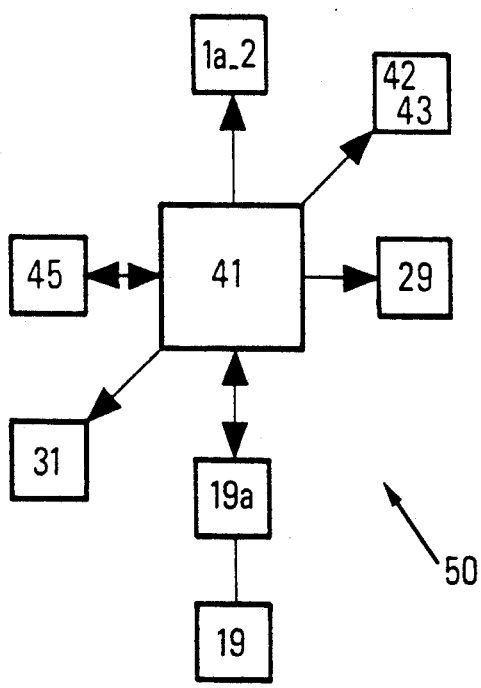

ON-LINE TEST AND ANALYSIS PROCESS AND EQUIPMENT MAKING IT POSSIBLE TO ESTABLISH A MATERIAL BALANCE OF A CHEMICAL REACTION

This application is a continuation of application Ser. No. 07/603,035, filed Oct. 25, 1990, now abandoned which is a divisional of U.S. patent application Ser. No. 06/875,167, filed Jun. 17, 1986, now U.S. Pat. No. 4,988,626, issued Jan. 29, 1991.

The invention relates to an on-line test and analysis process making it possible to establish a complete material balance of a chemical reaction, optionally in the presence of solid catalysts, particularly in divided form, making it possible to use, when applicable, only small amounts of these catalysts and to use them in standard refining and/or petrochemical processes. It also relates to equipment for implementing the process.

By way of example, the case of a process and equipment relating to a chemical reaction in the presence of a catalyst will be considered.

There are numerous types of devices making it possible to measure the activity of solid catalysts for the usual reactions encountered in the refining or petrochemical industry. These measurements are made under the following conditions:

pressure between $10^5$ and $3 \times 10^7$ pascals;

temperature between ambient and 750° C.;

liquid (hydrocarbons, other organic compounds) and/or gas (generally containing hydrogen) charge. The flow of charge, expressed in volume of charge per unit of catalyst and per hour (VPH), is generally between 0.01 and $10^2$ in the case of a liquid charge, between 10 and $10^5$ in the case of a gas charge;

shaped solid catalyst (balls, pellets, extrudates).

Although acceptable when it is desired to measure the activity of catalysts under conditions similar to or identical with those achieved in industrial installations, existing devices and particularly those operating at a pressure above atmospheric pressure exhibit a certain number of drawbacks:

the amounts of catalyst required at a minimum are a few cm$^3$, which can be a serious obstacle in the case of exploratory studies using catalysts whose preparation is difficult or expensive;

in standard installations, activation and bringing to normal operating conditions of certain catalytic systems is long (from several hours to several days), which is linked to the dimensions of the equipment (thermal inertia and large dead spaces);

for the same reasons, the period of a balance is necessarily important, which generally precludes detailed study of initial bringing to normal operating conditions of the catalytic system under consideration;

standard installations are generally not suited to an online automated analysis with a very short response time (size of dead spaces, inertias of the temperature and pressure regulating systems);

finally, complete automation of a standard installation and its control from a decentralized console is a complex and expensive operation.

The gains in accuracy and reliability that can be expected are limited for intrinsic reasons (lack of stability of the catalysts over long test periods) or extrinsic reasons (difficulties in getting free of the fluctuations in the settings of the various operating parameters).

Moreover, the patent U.S. Pat. No. 4,099,923 describes an automatic unit for catalyst preselection which makes it possible to obtain a preliminary indication of their potential activity. Further, the German publication DE 2.425.227 describes an automatic microreactor for the study of catalytic chemical reactions under pressure. But none of these documents suggest making a complete material balance of a chemical reaction under pressure by determining particularly the measurement of the output flow of the reactor, at the high temperature and pressure conditions of the reaction, a measurement that cannot be obtained directly.

There is also known and described in French patent 2.529.472 a catalytic microunit test device with a system of sampling valves transferred to one another over a gas chromatograph, which implies stopping the reactor particularly to avoid destruction of the catalyst. But this device does not make it possible to make a strict material balance because it does not have on-line analysis of the effluents under conditions of the reaction under pressure.

To succeed in knowing this output flow, it is necessary to determine the composition of the effluent at the output of the reactor, at the temperature and pressure conditions of the reaction. A first object of the invention therefore is to determine the volume composition of the effluent at the output of the reactor at the temperature and pressure conditions of the reaction and particularly at pressures above atmospheric pressure.

Another object of the invention is to establish from the knowledge of the composition of the charge, its flow and the flow of effluents at the output, a strict and complete material balance of a chemical reaction at a pressure above atmospheric pressure and at high pressure levels (for example, at a pressure above 60 bars).

Another object of the invention is to determine the material balance of a reaction by putting into play very small amounts of catalyst, in a repeatable manner, and in minimum time.

Another object of this invention is to eliminate the drawbacks mentioned above.

Another object is the evaluation of the catalytic properties of laboratory preparations without any particular shaping being necessary and with the possibility of being placed under initial kinetic conditions and/or of following rapid bringing to normal operating conditions or rapid deactivation.

To meet these objectives, an on-line test and analysis process is proposed making it possible particularly to establish a material balance of a chemical reaction during a determined period in which there is introduced into a reaction zone a charge, of known composition and flows, comprising at least a gas and/or at least a liquid and said charge is heated to a temperature and under a reaction pressure above atmospheric pressure in said zone to obtain an effluent totally in the gas phase; the process, moreover, is characterized by the following successive steps:

a) an aliquot of known volume of said effluent is sampled at said temperature and pressure, b) an analysis is made of said aliquot of said effluent sampled at said temperature and pressure, said aliquot containing at least one constituent, c) an expansion step to atmospheric pressure is performed to obtain an expanded effluent, d) an aliquot of known volume of the expanded effluent is sampled, e) an analysis is made of said aliquot of the expanded effluent, said aliquot containing at least in part said gas and/or at least in part said liquid of said charge and/or at least in part the constituent present in the sampled aliquot at said temperature and pressure, f) the total volume of said expanded effluent is measured during said determined period, and g) the material balance of said chemical reaction is deduced from the composition and flow of the charge as well as from the analysis made on the effluent sampled at said temperature and pressure of the reaction, from the analysis of the aliquot of the expanded effluent from the measurement of the volume of said expanded effluent.

By the term analysis is understood a qualitative and quantitative determination of the effluents, for example, by a gas chromatograph over a suitable column (capillary and/or packed). The chromatograph can also be coupled to a mass spectrometer.

It can be advantageous to heat the reaction zone to a temperature of 750° C., for example.

The new equipment, object of this invention, offers numerous advantages in relation to existing systems:

it is possible to test accurately small amounts of catalyst (down to some tens of mg, for example), without prior shaping (micronic powder, if necessary). Most samples of catalysts and particularly laboratory samples can therefore be studied;

the absence of significant thermal inertia, small dead spaces and on-line analysis (or with intermediate storage, for example, in heated ampoule) make it possible to study even fast bringing to normal operating conditions (less than one hour) and evaluate in a detailed way the activity and selectivity of a catalyst in a few hours (instead of several days);

it is possible to achieve a strict regulation (perfectly isothermal reactor, no charge loss, absence of fluctuations or drifts over the (short) periods necessary for a complete catalytic test). Moreover, by automation of the installation described in the invention, the reproducibility of the tests is much greater than that available on standard installations, which makes possible an effective comparison between catalysts that are close in activity and selectivity.

After the expansion stage, it can be particularly advantageous to perform a condensation step (low pressure) which delivers a condensate that is taken into account in the material balance to the extent that it is possible to weigh it and determine its composition. When the conversion rates are high (>10%), the presence of heavy condensates can lead to performing an additional condensation step before step a). The condensate is analyzed qualitatively and quantitatively and is taken in account in the material balance.

The invention also relates to a device for using the process, which comprises the following combination:

a reactor, a system for injection of a charge, connected to said reactor, means for measuring the flow and composition of said charge, a means for heating said reactor, this latter delivering an effluent totally in gas phase, at least a sampling valve provided with heating elements, this valve being connected to the output of the reactor and containing an aliquot of said effluent, a first analysis means such as a gas chromatograph for qualitative and quantitative analysis of said effluent contained in said valve, this first analysis means being connected to said valve, an expansion means at the output of the first analysis means delivering an expanded effluent, an additional sampling valve provided with a heating element to contain an aliquot of the expanded effluent, a second analysis means such as a gas chromatograph for qualitative and quantitative analysis of said aliquot of the expanded effluent, said second analysis means being connected to said additional sampling valve, a means for measuring the volume of said expanded effluent, connected to the output of said second analysis means, and processing means connected to said means for measuring the flow and composition of the charge, to said means for measuring the volume and to said first and second analysis means, these processing means being suitable for determining a material balance from the measurements of flow and composition of the charge, from the measurement of volume and from the analysis of said expanded effluent as well as from the analysis of the effluent totally in gas phase.

The set of these valves samples only a minute amount of product (a few microliters) necessary for chromatographic analysis.

According to another embodiment, the equipment can comprise a first condensation means at the output of the expansion means, which makes it possible to analyze the condensate and to analyze the uncondensed expanded gas effluent.

The second analysis means is generally the same as the first analysis means with another chromatographic column and another detector which can be identical with those of the first analysis means.

According to another particular embodiment making it possible to analyze the effluent for high conversion rates (>10%), the equipment can comprise at least a second condensation means located between the output of the reactor and the sampling valves.

The processing means comprise a programmable controller suitable for regulating and setting a group of means connected to the controller, these means comprising particularly:

a) the means for measuring the flow and composition of the charge, b) the means for measuring the temperature of the reactor as well as those of the heating means, c) the expansion means, and d) the first and second condensation means.

BRIEF DESCRIPTION OF THE DRAWINGS

The invention will be better un( ith reference to the figures presented below, of which:

FIG. 1 represents the equipment according to the invention;

FIG. 2 illustrates a diagram of the sampling valves and analysis zone; and

FIG. 3 shows the processing means according to the invention which work together for determination of the test and information desired.

In FIG. 1 representing a particular embodiment, the equipment according to the invention generally comprises a feeding or injection stage 1, a reaction stage 11 comprising a preheating unit 4 and reactor 5, an analysis zone 20 comprising a gas chromatograph 19, a set of sampling valves 21, 24 and specific chromatographic columns suitable for the analysis to be performed, an expansion means 29 with or without phase separator 30 and volumetric apparatus 31 for measuring the output flows and total volume of the expanded effluent.

The reagents constituting the charge and in gas form are injected by at least a mass flow regulator 1a with a 1% accuracy and homogenized in a mixer 3 while liquid reagents of the charge are injected by a line 2a with at least a syringe pump 2 at the desired pressure and flows (accuracy of $10^{-3}$ ml for a flow range of 0.2 to 100 ml/hour).

The liquid is preheated and vaporized at the level of upper zone 4 which constitutes the preheater. This latter consists of a metal pin which receives a fine tube wound around its lower end, whose upper end is located opposite the gas intake. The liquid vaporized in the hot zone of preheater 4 is entrained directly by the gases and the whole is homogenized, on the one hand, by the continuous vaporization and the joint arrival of the gases, the space velocity being very great. The whole is expanded in an inert material filling zone (quartz grains, for example).

At the output of preheater 4 is located reactor 5 itself in tubular form which can be heated like the preheater to a temperature of 750° C. by a heating means such as a furnace 6 with very slight thermal inertia. This latter actually comprises two cylindrical half-shells 12 containing resistors 13, regulation thermocouples 14 and monitoring thermocouples 14a as well as outside metal fins 15 assuring ventilation or cooling of the reactor.

The resistors are very close to the reactor (about 1 mm) and are the shielded type, vacuum-brazed in longitudinal grooves or fastened to cylindrical half-shells by spraying of molten metal (Schoop process). Moreover, no refractory material between the half-shells and reactor hamper the dissipation of excess calories. The furnace-reactor unit is programmed and regulated automatically by programming and regulating means 42.

Reactor 5 (10 mm in inside diameter) comprises approximately along its longitudinal axis an insertion pyrometer 17 (about 3 mm in outside diameter) where regulation thermocouples 14 and monitoring thermocouples 14a are placed. According to a preferred embodiment, the regulating thermocouples on resistors 13 are approximately at the same level as those placed on the reactor.

The furnace, moreover, is machined from refractory steel type Incoloy 800 (750° C.), the reactor and insertion pyrometer 17 which it contains are of special steel of the same type, optionally gold-covered and diffusion-tight.

Reaction zone 18 itself directly following preheater 4 consists of an annular space between the wall of the reactor and pyrometer 17.

The effluent from the reaction is directed to analysis zone 20 due to a T-coupling 8 at the output of the reactor which receives insertion pyrometer 17 and thanks to a heated line 9 with a small dead space (inside diameter:0.57 mm, for example) and regulated by regulation means 43. The effluent therefore is always at the temperature and pressure of the reaction. Analysis zone 20 consists of a gas chromatograph 19 (first analysis means) comprising sampling valves suitable for working under temperature and pressure; (21, 22, 23, FIG. 2) placed in series whose number varies as a function of the type of constituents to be analyzed, for example from 2 to 8 and which are able to isolate, in a capacity of known volume, a certain amount of effluents which will be analyzed jointly over the various chromatographic columns (40 represented in FIG. 2) equipped with different detectors; (25, 26, 27, FIG. 2). Thus, for example, the on-line analyzer comprising a mixture of hydrogen, water and aliphatic alcohol comprises three valves 21, 22 and 23 and three columns (packed or capillary) of which two are equipped with a thermal conductivity detector 25 and 26 and the third with a flame ionization detector 27 as shown in FIG. 2.

At the output of the sampling valves, the effluent is directed, since it is still under pressure, over an expansion means 29 which comprises a pressure sensor coupled to a solenoid valve (Brooks type) which regulates at the reaction pressure and expands the effluent to atmospheric pressure. Optionally, according to another embodiment, a liquid phase which was able to appear during expansion is separated thanks to a first condensation means or low-pressure separator 30 and analyzed separately by simple weighing and chromatography. The gas effluent at atmospheric pressure is then directed by a line 10 to an additional sampling valve 24 at atmospheric pressure. This valve is mounted in series and is provided with heating elements. The effluent circulates in another chromatographic column 40 (second analysis means) where the answer is provided by a thermal conductivity or flame ionization detector 28 depending on the need. This last analysis makes it possible by comparison with the analysis made at the output of the reactor to go back to the gas flow at the output of the reactor and therefore to calculate the material balances in a strict manner. At the output of the chromatograph, this same gas effluent at atmospheric pressure is directed by a line 44 to a means 31 for measuring the volume of the expanded effluent consisting of a cylinder 32 equipped with a fluid-tight piston 33 with a mercury seal, operated by a gearmotor (not shown in FIG. 1), itself coupled to a differential sensor. For a slight variation of pressure in the cylinder (35 mbar) the sensor triggers the movement of the piston. Thus it is possible to follow the expanded gas flow at the output of the reactor.

Calculation of a material balance implies a knowledge of the volume flow of the charge and its composition at the input of the reactor, and also the volume flow and composition of the effluent at the output of the reactor at the temperature and pressure conditions of the reaction.

Generally an arrangement is made so that the analyses (for example, an analysis of the constituents of the effluent at the temperature and pressure conditions of the reaction and analysis of the expanded effluent) comprise at least a common constituent which allows the link between at least two analyses and to determine the volume composition of the effluent at the output of the reactor.

Starting from the difference between the input flow and output flow of the expanded effluent corresponding to the volume of gas which has reacted and the volume composition thus obtained, it is possible to determine the material balance of the reaction by reference to the composition and to the flow of the charge.

Starting from the volume composition at the reaction conditions, and from the volume flow at the output of the reactor, there is determined, according to calculations known to a man of the art, the average molecular weight of the effluent, therefore its mass, and there is deduced therefrom the weight of the output effluents which is compared with the weight of the charge at the input to determine the material balance, which leads to a mass balance. It is also possible to express the balance in a different way: carbon, hydrogen, oxygen balances, as in the examples below.

In case it is desired to monitor perfectly the composition of the gas mixture constituting the charge, coming from mixer 3, it is possible, according to another embodiment, to inject by a line 7 this gas mixture which will then go through a three-way valve 36 (FIG. 2) and by sampling valves 21, 22 and 23, making possible the analysis on specific chromatographic columns. Depending on the case, three-way valve 36 will make it possible therefore to direct the charge before reaction (line 7) or the gas effluent after reaction (lines 9, 34, 35, FIG. 2) to the on-line analyzer.

According to an advantageous embodiment when great conversion rates are involved (for example, greater than 10%) which make it possible to obtain heavier effluents, this device can be equipped with a second condensation means or high-pressure separator 37 at the output of reactor 5, in which the heavy constituents are condensed at the desired temperature, their liquid level is regulated by a differential sensor (not shown) coupled to a motorized microvalve. The liquid phase thus collected is analyzed separately by weight and chromatography, while the gas phase is directly injected by a line 34 and three-way valve 36 into the circuit of valves 21, 22, 23 and 24 of the analysis zone and analyzed as above.

Finally, according to a last embodiment, during studies of initial kinetics where the evolution of the conversion is examined at close intervals, sampling valves 38 can be inserted between the output of reactor 5 and analysis zone 20 and can make it possible to sample and isolate the effluent at the temperature and pressure conditions of the reaction, which is then transferred at the desired moment by a line 35 to the analysis zone while the untrapped scent is analyzed as above.

Processing means 50 (FIG. 3) comprise particularly a programmable controller 41 (type PB 400 of Merlin Gerlin) to regulate and adjust a group of means connected to said controller, the means comprising means 1a, 2 for measuring input flows of the charge (liquid and/or gas), means 42, 43 for measuring the temperature of the furnace-reactor unit and lines, expansion means 29 as well as first 30 and second 37 condensation means. It further makes possible the monitoring and start of means 31 for measuring the volume of the expanded effluent. Further, the controller is coupled directly to the chromatograph (analysis means 19) itself programmed to perform analyses as well as control of the valves, and equipped with a computer 19a itself connected to the controller for dialogue (for example, dialogue parameter: conversion). Finally, the controller manages the various safety aspects (limiting temperature, leak of flammable or toxic substances) 45.

It would not be going outside of the scope of the present invention to cause the intervention at the output of volumetric apparatus 31 of another measuring apparatus (UV, IR or mass spectrometer, for example).

This system, object of the present invention, can be used for multiple applications, particularly:

A) in refining:
catalytic cracking
hydrocracking
reforming
hydroisomerization
hydrogenation
B) in petrochemistry
transformation of aromatics (isomerization, disproportionation, hydrodealkylation),
various oxidations (oxidation of toluene to benzaldehyde, methanol to formol).
C) in $CO + H_2$ chemistry (synthesis gas treatment) synthesis of methanol conversion of methanol to hydrocarbons conversion of $CO + H_2$ to higher alcohols.

This invention is, in particular, very useful for following the bringing to normal operating conditions of a catalyst.

The following examples illustrate the invention:

EXAMPLE 1

It relates to the kinetic study of synthesis of alcohols from $H_2$ and CO on a zinc aluminate catalyst doped with copper and cobalt, alkalized by NAOH.

This catalyst was brought to normal operating conditions during 20 hours after a reduction to 500° C. by hydrogen.

A known volume of the charge, generally equal to 16 microliters ($16 \times 10^{-6}$ l) was sampled by sampling valve 21 and directed over a chromatographic column of molecular sieve 13X (80–100 mesh) 3 meters in length, with an inside diameter of 2 mm, heated to 70° C. in isotherm.

Once separated, the constituents of the charge were detected by a thermal conductivity detector (TCD); they were in a volumetric ratio $H_2/CO$ equal to 2.

The volume flow at the input of the reactor at normal temperature and pressure (T,P,N) was 1.55 l/h.

There was introduced into the reactor the charge of determined composition the volume of which per unit of weight of catalyst and per hour VPH was 600 ml/g/h, and the catalyst (0.1 g, grain size $100 \times 10^{-6}$ m).

The reaction conditions were the following:

| T: 280° C. | $P = 7 \times 10^6$ Pa. |
|---|---|

The effluents of the reaction were analyzed immediately by the gas chromatograph at reaction conditions after a known volume of 16 microliters (TPN) ($16 \times 10^{-6}$ l) was sampled in valves 21, 22 and 23 at the reaction conditions.

The effluents $H_2$, CO were analyzed from valve 21 as above (table 1).

TABLE 1

| Compounds | Composition Volume % |
|---|---|
| $H_2$ | 67.10 |
| CO | 32.90 |

The effluents CO, $CO_2$, $H_2O$, $C_1OH$, DME and $CH_4$ were analyzed from valve 22 over a Chromosorb 102 column (80–100 mesh) with a length of 3 m and inside diameter of 2 mm at 70° C. in isotherm, associated with a thermal conductivity detector (table 2).

TABLE 2

| Compounds | Composition Volume % |
|---|---|
| CO | 92.47 |
| $CO_2$ | 2.93 |
| $H_2O$ | 0.69 |
| DME | 0.06 |
| $CH_4$ | 1.97 |
| $C_1OH$ | 1.88 |

The effluents $CH_4$, hydrocarbons $C_2$ to $C_{10}$, $C_1OH$, $C_2OH$, $C_3OH$, etc ... were analyzed from valve 23 over a capillary chromatographic column SiL 8 of 50 m in length, 0.22 mm in inside diameter, phase thickness $0.12 \times 10^{-6}$ m and at a programmed temperature of 20° C. to 250° C., associated with a flame ionization detector (table 3).

TABLE 3

| Compounds | Composition Volume % |
|---|---|
| DME | 1.22 |
| $CH_4$ | 41.46 |
| hydrocarbons $C_2$ to $C_{10}$ | 11.58 |
| $C_1OH$ | 39.63 |
| $C_2OH$ | 4.88 |
| $C_3OH$ | 1.23 |

After analysis at reaction conditions, the effluent was expanded at atmospheric pressure. A known volume of 100 microliters ($100 \times 10^{-6}$ l) (T,P,N) was sampled by valve 24 and the aliquot of the effluent was analyzed over a molecular sieve column 13×identical with the preceding one (table 4).

TABLE 4

| Compounds | Composition Volume % |
|---|---|
| $H_2$ | 67.13 |
| CO | 32.87 |

Starting form a constituent common to the analyses of the expanded effluent and the effluent at reaction conditions, CO, for example, chosen in table 4 and in table 2, it was possible to calculate a parameter corresponding for example to hydrogen resulting from another analysis, the one presented in table 2 and so on for all the other constituents.

Thus the volume composition of the mixture was calculated at reaction conditions which is shown in table 5 test 1.

TABLE 5

| Compounds | Composition Volume % | | |
|---|---|---|---|
|  | 1 | 2 | 3 |
| $H_2$ | 65.19 | 65.26 | 65.45 |
| CO | 31.92 | 31.93 | 31.60 |
| $CO_2$ | 1.01 | 1.02 | 1.00 |
| $H_2O$ | 0.24 | 0.20 | 0.25 |
| DME | 0.02 | 0.01 | 0.01 |
| $CH_4$ | 0.68 | 0.69 | 0.70 |
| $C_2$ to $C_{10}$ (hydrocarbons) | 0.19 | 0.18 | 0.19 |
| $C_1OH$ | 0.65 | 0.64 | 0.70 |
| $C_2OH$ | 0.08 | 0.06 | 0.08 |
| $C_3OH$ | 0.02 | 0.01 | 0.02 |

Starting from the volume flow of the expanded effluent measured at the temperature and normal pressure conditions and equal to 1.42 l/h, from the volume composition at reaction conditions, from the composition of the charge and from its volume flow, the material balance was deduced therefrom whose errors were the following:

| mass balance ratio | −0.41% |
|---|---|
| C/H | 1.56% |
| C/O | 0.40% |
| O/H | 1.15% |
| carbon balance | $-1.21 \times 10^{-2}$% |
| hydrogen | −1.55% |

| oxygen | −0.41% |
|---|---|

A reproducibility test relating to three average conversion balances (8.86%) performed under the same conditions as this example 1 with the same lot of catalyst is shown in table 5.

The errors on the mass balance (C, H, O) are approximately the same in the three cases. The period of determination of the balance is from about 30 minutes to 1 hour.

When the reaction is performed in a catalytic test development unit with the same catalyst of example 1 and when the balance is calculated from samples taken from the unit, a margin of error of the balance on the order of 5% is obtained for a conversion rate comparable to that of example 1.

EXAMPLE 2

Example 1 was repeated with the same catalyst brought to normal operating conditions during 10 hours after a hydrogen reduction to 500° C.

The operating conditions remained the same, except:
VPH = 18000 ml/g/h
volume flow at input (TPN): 4.60 l/h The analytic results for a small conversion rate are shown in table 6.

TABLE 6

| Compounds | Composition Volume % |
|---|---|
| $H_2$ | 66.85 |
| CO | 32.63 |
| $CO_2$ | 0.18 |
| $CH_4$ | 0.8 |
| $C_2H_6$, $C_3H_8$, $C_4H_{10}$ | 0.02 |
| $C_1OH$ | 0.24 |
| $C_2OH$ | 0.003 |

The conversion obtained was: 2.16%. The volume flow of the expanded effluent was: 4.49 l/h. The errors in the balance were the following:

| mass balance | −0.21% |
|---|---|
| C/H | −1.80% |
| C/O | −0.19% |
| O/H | −1.59% |
| carbon balance | −0.5% |
| $H_2$ | +1.27% |
| $O_2$ | −0.34% |

These results with the above accuracy cannot be obtained on a standard catalytic test development unit with as small a conversion rate.

EXAMPLE 3

Example 1 was repeated, the operating conditions remaining the same (the input volume flow varying very slightly: 1.50 l/h but the liquid fraction of the effluents was collected thanks to a high-pressure separator, weighed and analyzed independently by gas chromatography, the uncondensed phase being subjected to the same analyses as that of example 1.

The volume compositions are shown in table 7.

TABLE 7

| Compounds | Composition Volume % | |
|---|---|---|
| | 1 Uncondensed | 2 Condensed |
| $H_2$ | 65.20 | 65.00 |
| CO | 31.90 | 32.00 |
| $CO_2$ | 1.00 | 1.04 |
| $H_2O$ | 0.24 | 0.25 |
| DME | 0.02 | 0.02 |
| $CH_4$ | 0.68 | 0.70 |
| $C_2$ to $C_4$ (hydrocarbons) | 0.15 | 0.14 |
| $C_5$ to $C_{10}$ (hydrocarbons) | 0.05 | 0.05 |
| $C_1OH$ | 0.66 | 0.70 (Condensed) |
| $C_2OH$ | 0.08 | 0.08 |
| $C_3OH$ | 0.02 | 0.02 |

The conversion obtained was 9%.

The volume flow of the expanded effluent was 1.36 l/h. The errors in the balance were the following:

| mass balance ratio | −0.4% |
|---|---|
| C/H | +1.5% |
| C/O | +0.40% |
| O/H | +1.0% |
| carbon balance | −0.02% |
| hydrogen | −1.40% |
| oxygen | −0.40% |

We claim:

1. On-line test and analysis equipment suitable for establishing a material balance of a chemical reaction, comprising:
    a reactor;
    an injection system for a charge having a certain flow and composition, connected to the reactor;
    means for measuring the flow and composition of the charge;
    means to heat the reactor so as to provide a gaseous effluent;
    first analysis means to provide a qualitative and quantitative analysis of the composition of the gaseous effluents;
    expansion means for the effluents;
    a second analysis means for expanded effluent to provide a qualitative and quantitative analysis of the composition of the expanded effluent;
    means to measure the volume of the expanded effluents connected to the expansion means; and
    processing means connected to said means for measuring the flow and composition of the charge, to said means for measuring the volume, and to said first and second analysis means, said processing means being capable of determining a material balance from the measurements of flow and composition of the charge and the analysis of the charge, and from the analysis of the effluents.

2. Equipment according to claim 1, wherein said regulatable expansion means comprises a pressure sensor and a solenoid valve.

3. On-line test and analysis equipment suitable for establishing a material balance of a chemical reaction, comprising:
    a reactor (5) having an outlet,
    a system (1) for injection of a charge having a certain flow and composition, connected to said reactor,
    means (1a, 2) for measuring the flow and composition of said charge,
    means (6) for heating said reactor, to provide a totally gaseous effluent,
    at least one sampling valve (21) provided with heating elements, said sampling valve being connected to the output of reactor (5) and containing an aliquot of said effluent,
    first analysis means (19) having an outlet for qualitative and quantitative analysis of the composition of said effluent contained in said sampling valve, said first analysis means being connected to said sampling valve,
    regulatable expansion means (29) at the output of the first analysis means (19) for delivering an expanded effluent,
    an additional sampling valve (24) provided with a heating element, for containing an aliquot of the expanded effluent,
    second analysis means (19, 28) having an outlet for qualitative and quantitative analysis of the composition of said aliquot of the expanded effluent, said second analysis means being connected to said additional sampling valve,
    means (31) for measuring the volume of said expanded effluent, connected to the output of said second analysis means (19, 28), and
    processing means (50) connected to said means (1a, 2) for measuring the flow and composition of the charge, to said means for measuring the volume (31) and to said first and second analysis means (19 and 19, 28), said processing means being capable of determining a material balance from the measurements of flow and composition of the charge, from the measurement of volume and from the analysis of said expanded effluent in said second analysis means as well as from the analysis of the effluent totally in gas phase in said first analysis means.

4. Equipment according to claim 3, wherein said second analysis means is a gas chromatograph.

5. Equipment according to claim 3, wherein said regulatable expansion means comprises a pressure sensor and a solenoid valve.

6. Equipment according to claim 3, wherein said processing means (50) comprises a programmable controller suitable for regulating and setting a group of means connected to said controller (41), said means comprising (FIG. 3):
    a) said means (1a, 2) for measuring the flow and composition of the charge,
    b) means (42, 43) for measuring the temperatures of reactor (5) and heating means (6),
    c) said expansion means (29), and
    d) first (30) and second condensation means (37).

7. Equipment according to claim 5, wherein said processing means (50) comprises a programmable controller capable of regulating and setting a group of means connected to said controller (41), said means comprising (FIG. 3):
    a) said means (1a, 2) for measuring the flow and composition of the charge,
    b) means (42, 43) for measuring the temperatures of reactor (5) and heating means (6),
    c) said expansion means (29), and
    d) first (30) and second condensation means (37).

8. Equipment according to claim 3, wherein said first analysis means is a gas chromatograph.

9. Equipment according to claim 8, wherein said second analysis means is a gas chromatograph.

10. Equipment according to claim 3, further comprising a first condensation means (30) located between said expansion means (29) and said second analysis means (19, 28) of the expanded effluent.

11. Equipment according to claim 10, wherein said processing means (50) comprises a programmable controller capable of regulating and setting a group of means connected to said controller (41), said means comprising (FIG. 3):
  a) said means (1a, 2) for measuring the flow and composition of the charge,
  b) means (42, 43) for measuring the temperatures of reactor (5) and heating means (60),
  c) said expansion means (29), and
  d) first (30) and second condensation means (37).

12. Equipment according to claim 10, further comprising at least a second condensation means (37) located between the output of reactor (5) and said at least one sampling valve (21 and 24, FIG. 2).

13. Equipment according to claim 12, wherein said processing means (50) comprises a programmable controller capable of regulating and setting a group of means connected to said controller (41), said means comprising (FIG. 3):
  a) said means (1a, 2) for measuring the flow and composition of the charge,
  b) means (42, 43) for measuring the temperatures of reactor (5) and heating means (6),
  c) said expansion means (29), and
  d) first (30) and second condensation means (37).

* * * * *